(12) United States Patent
Habicht et al.

(10) Patent No.: US 11,771,850 B2
(45) Date of Patent: Oct. 3, 2023

(54) VAPORIZER POD FILTRATION SYSTEMS

(71) Applicant: SV3, LLC, Phoenix, AZ (US)

(72) Inventors: Geoff Habicht, Phoenix, AZ (US); Amir Hakak, Phoenix, AZ (US)

(73) Assignee: SV3, LLC, Phoenix, AZ (US)

( * ) Notice: Subject to any disclaimer, the term of this patent is extended or adjusted under 35 U.S.C. 154(b) by 967 days.

(21) Appl. No.: 16/445,079

(22) Filed: Jun. 18, 2019

(65) Prior Publication Data

US 2020/0397057 A1 Dec. 24, 2020

(51) Int. Cl.
| | |
|---|---|
| *A24F 40/10* | (2020.01) |
| *A24F 40/42* | (2020.01) |
| *A24F 40/485* | (2020.01) |
| *A61M 11/04* | (2006.01) |

(52) U.S. Cl.
CPC ..... *A61M 11/042* (2014.02); *A61M 2205/125* (2013.01); *A61M 2205/8206* (2013.01)

(58) Field of Classification Search
CPC ..... A24F 40/10; A24F 40/485; A61M 11/042; A61M 2205/125; A61M 2205/8206
See application file for complete search history.

(56) References Cited

U.S. PATENT DOCUMENTS

| | | | | |
|---|---|---|---|---|
| 5,470,511 | A * | 11/1995 | Laybourne | A61M 16/183 |
| | | | | 128/204.12 |
| 8,925,555 | B2 * | 1/2015 | Monsees | A24F 40/40 |
| | | | | 131/194 |
| 10,206,428 | B2 * | 2/2019 | Thorens | A24F 40/40 |
| 10,244,790 | B1 * | 4/2019 | Christie | A24F 7/04 |
| 10,869,507 | B2 * | 12/2020 | Zheng | A24F 40/48 |
| 11,000,072 | B2 * | 5/2021 | Xu | A24F 40/30 |
| 11,191,303 | B2 * | 12/2021 | Fu | H05B 3/44 |
| 11,219,245 | B2 * | 1/2022 | Liu | A24F 40/40 |
| 11,253,002 | B2 * | 2/2022 | Zhang | A24F 40/485 |
| 2018/0242644 | A1 * | 8/2018 | Bessant | H05B 3/34 |
| 2018/0343920 | A1 * | 12/2018 | Sutton | A24F 40/30 |
| 2019/0166913 | A1 * | 6/2019 | Trzecieski | A61M 15/06 |
| 2020/0022413 | A1 * | 1/2020 | Zhang | A24F 40/485 |
| 2020/0077696 | A1 * | 3/2020 | Williams | A24D 3/048 |
| 2020/0077704 | A1 * | 3/2020 | Ouyang | H05B 3/44 |
| 2020/0138113 | A1 * | 5/2020 | Rosser | A61M 11/042 |
| 2020/0221778 | A1 * | 7/2020 | Trzecieski | A24F 40/10 |
| 2020/0383382 | A1 * | 12/2020 | Yu | A24F 42/80 |
| 2021/0368868 | A1 * | 12/2021 | Trzecieski | A24F 40/51 |
| 2022/0030942 | A1 * | 2/2022 | Lord | A24F 40/44 |

* cited by examiner

*Primary Examiner* — Abdullah A Riyami
*Assistant Examiner* — Thang H Nguyen
(74) *Attorney, Agent, or Firm* — Snell & Wilmer L.L.P.

(57) ABSTRACT

A vaporizer pod comprises a reservoir defined by, and disposed within a housing, wherein the housing defines a central channel extending between a central channel inlet and a central channel outlet, a column disposed within the housing, an atomizer channel extending between an atomizer channel inlet and an atomizer channel outlet, a heat conductor disposed within the column, and a heat-conducting filter disposed within the column.

20 Claims, 7 Drawing Sheets

VAPORIZER POD FILTRATION SYSTEMS

FIELD OF THE INVENTION

The present invention relates to vaporizer pods and, in particular, to vaporizer pods having heat-conducting filters.

BACKGROUND OF THE INVENTION

Vaporizers are typically used to aerosolize liquids or the volatile substances contained in solid or semisolid substances, such as extracts. During operation, these devices typically require a user to draw air into a chamber of the device where the liquid or extract is heated. This air is then drawn into the user's mouth along with the aerosolized liquids or volatile substances generated by heating the liquid or extract. In such systems, liquid may spill into the user's mouth if the vaporizer is tipped or held in any position other than vertically. In such systems, extract may solidify in a position that obstructs airflow, causing the user to apply increased suction; when the blockage releases, portions of the extract may be drawn into the user's mouth. Spills or introduction of liquids and/or extract into the user's mouth may cause an unpleasant taste, mouth burns, and/or waste of the liquid or extract. In certain devices, a cotton gauze is disposed in the vaporizer to block spills of liquid and extract. However, such cotton gauze absorbs and wastes liquid and extract, decreases the concentration of vapor introduced to the user's mouth, and impairs the vapor's flavor. Accordingly, new and improved vaporizer pods are needed.

SUMMARY

In various exemplary embodiments, the present invention is directed to a vaporizer pod comprising a reservoir defined by, and disposed within a housing, wherein the housing defines a central channel extending between a central channel inlet and a central channel outlet, a column disposed within the housing, an atomizer channel extending between an atomizer channel inlet and an atomizer channel outlet, a heat conductor disposed within the column, and a filter disposed within the column.

In various embodiments, the atomizer channel is defined by the housing and the column. In various embodiments, the central channel outlet and the atomizer channel outlet are disposed in a mouth piece. In various embodiments, the vaporizer further comprises a fill plug coupled to and disposed at least partially within a fill aperture defined by the housing. In various embodiments, the fill plug is coupled to and disposed at least partially within a fill aperture defined by a base portion of the housing. In various embodiments, the fill plug is coupled to and disposed at least partially within a fill aperture defined by a side wall of the housing. In various embodiments, a base portion of the housing defines at least a portion of the reservoir, and wherein the column is disposed at least partially within the base portion. In various embodiments, the reservoir is in fluid communication with the heat conductor through a first fluid port defined by the column. In various embodiments, the atomizer channel inlet is in fluid communication with the atomizer channel outlet through a second fluid port defined by the column. In various embodiments, the filter is coupled to and disposed within an upper portion of the column.

In various embodiments, the filter comprises a heat-conducting material. In various embodiments, the filter comprises a porous mesh. In various embodiments, the filter comprises a metal. In various embodiments, the filter comprises a ceramic. In various embodiments, the heat conductor comprises a wire. In various embodiments, the heat conductor may comprise a coil. In various embodiments, the heat conductor may be a hollow cylindrical shape.

In various exemplary embodiments, the present invention is directed to a vaporizer pod comprising a reservoir defined by, and disposed within a housing, wherein the housing comprises a central channel inlet, a central channel outlet, and a central channel disposed therebetween and defined by the housing, and an atomizer channel inlet, an atomizer channel outlet, and an atomizer channel disposed therebetween, wherein the atomizer channel is defined by the housing and a column disposed within the housing, and wherein the central channel outlet and the atomizer channel outlet are disposed in a mouth piece. In various embodiments, the vaporizer pod further comprises a heat conductor disposed within the column, wherein the heat conductor is in fluid communication with the reservoir and in electrical communication with a contact, a heat-conducting filter disposed within the column, and a fill plug coupled to and disposed at least partially within a fill aperture defined by the housing.

In various exemplary embodiments, the present invention is directed to a vaporizer comprising a battery in electrical communication with a contact of a vaporizer pod, wherein the vaporizer pod comprises a reservoir defined by, and disposed within a housing. In various embodiments, the housing comprises a central channel inlet, a central channel outlet, and a central channel disposed therebetween and defined by the housing, and an atomizer channel inlet, an atomizer channel outlet, and an atomizer channel disposed therebetween and defined by the housing and a column disposed within the housing, wherein the central channel outlet and the atomizer channel outlet are disposed in a mouth piece. In various embodiments, the vaporizer pod further comprises a heat conductor disposed within the column, wherein the heat conductor is in fluid communication with the reservoir and in electrical communication with the contact, a heat-conducting filter disposed within the column, and a fill plug coupled to and disposed at least partially within a fill aperture defined by the housing.

BRIEF DESCRIPTION OF THE DRAWINGS

The accompanying drawings are included to provide a further understanding of the present disclosure and are incorporated in, and constitute a part of, this specification, illustrate various embodiments, and together with the description, serve to explain the principles of the disclosure.

DETAILED DESCRIPTION OF THE INVENTION

Figure 1:
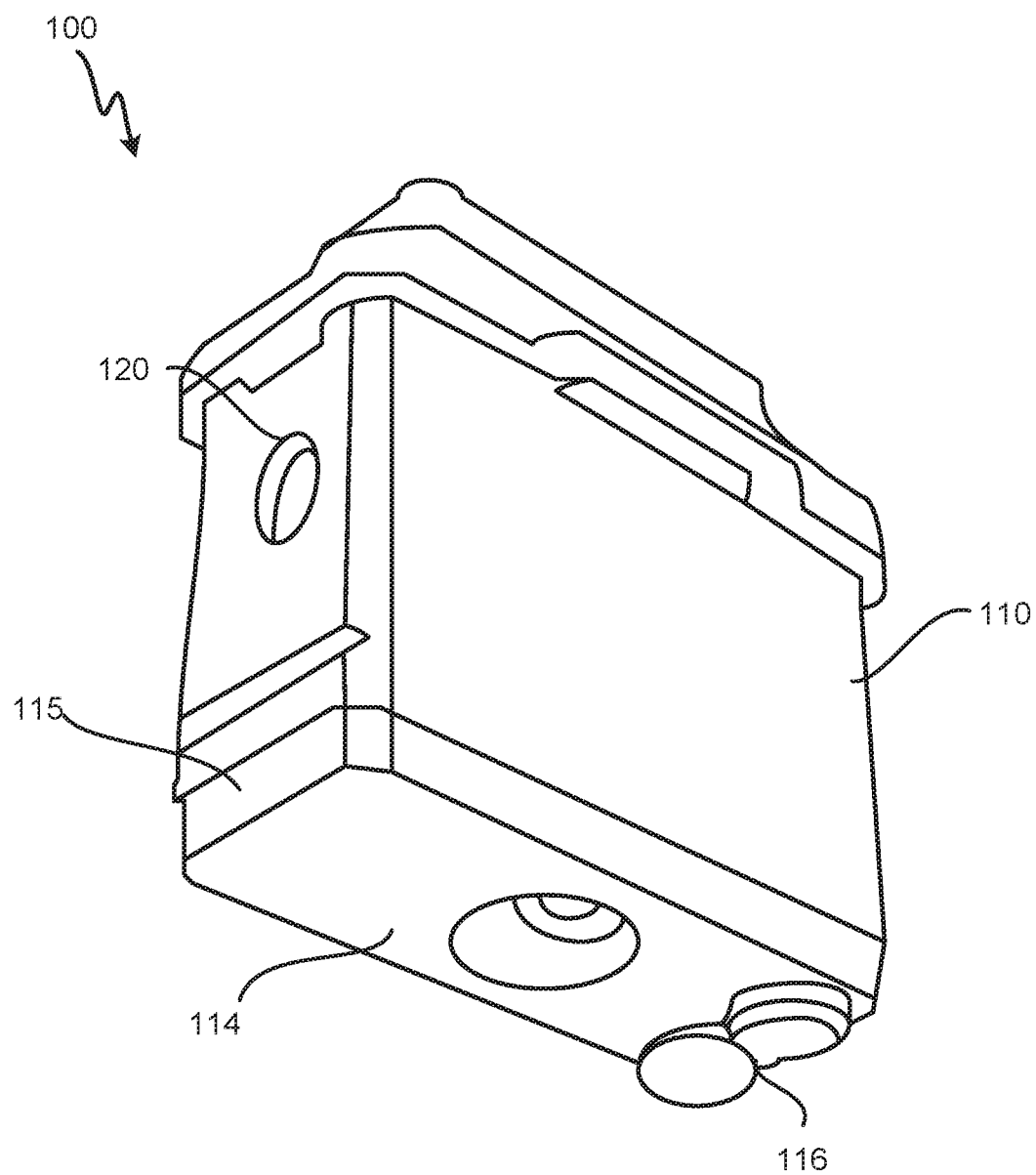
FIG. 1 illustrates a perspective view of a vaporizer pod in accordance with various embodiments.

The following description is of various embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure or appended claims.

The detailed description of exemplary embodiments herein makes reference to the accompanying drawings and pictures, which show various embodiments by way of illustration. While these various embodiments are described in sufficient detail to enable those skilled in the art to practice the disclosure, it should be understood that other embodiments may be realized and that logical and/or functional changes may be made without departing from the spirit and scope of the disclosure. Thus, the detailed description herein is presented for purposes of illustration only and not of limitation. Any reference to singular includes plural embodiments, and any reference to more than one component may include a singular embodiment.

Vaporizer systems and devices are provided. In the detailed description herein, references to "an exemplary embodiment," "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

For the sake of brevity, conventional vaporizers and vaporizer components may not be described in detail herein. Furthermore, the connecting lines shown in various figures contained herein are intended to represent exemplary functional relationships and/or physical or communicative couplings between various elements. It should be noted that many alternative or additional functional relationships or physical or communicative connections may be present in a practical vaporizer system.

In various embodiments, a vaporizer pod is disclosed herein. The vaporizer pod may be configured to heat liquids and extracts at a temperature such that volatile substances contained in the liquids and extracts are aerosolized or otherwise heated without combustion. In various embodiments, the vaporizer pod may be compatible for use in a portable vaporizer, vaporizer pen, table-top vaporizer, e-liquid vaporizer, standard vaporizer, box vaporizer, whip-style vaporizer, forced air vaporizer, or any other suitable type of vaporizer.

The vaporizer pod disclosed herein may be configured to direct two, separated air flows simultaneously into a user's mouth during operation of a vaporizer coupled to the vaporizer pod. A first air flow may direct ambient air inside an atomizer channel inlet from outside the vaporizer pod, to, near, and/or through a heating element, and subsequently to, near, and/or into a user's mouth via an atomizer channel outlet. The heating element may be in contact with liquids and extracts disposed within the vaporizer pod. Application of heat by the heating element may cause evaporation, sublimation, volatilization, atomization, and/or aerosolization of all or a portion of the liquid or extract such that it is carried by the heated first air flow to, near, and/or into a user's mouth via the atomizer channel outlet. As used herein, "vapor" may comprise aerosolized liquids and/or extracts. A second air flow may direct ambient air inside a central channel inlet from outside the vaporizer pod, through the vaporizer pod via the central channel, and to, near, and/or into the user's mouth via the central channel outlet. The two air flows in communication with the atomizer channel outlet and central channel outlet may be directed into the user's mouth via a mouth piece upon the user inhaling from the mouth piece.

In various embodiments, the second air flow may mix with the first air flow near or inside the central channel upon the user's inhalation into the mouth piece. In various embodiments, the first air flow, traveling from the atomizer channel inlet and passing through the heating element before passing into the user's mouth via the atomizer channel outlet, may be a high temperature, depending on the temperature provided by the heating element. In various embodiments, the temperature of the second air flow, traveling from the central channel inlet through the central channel, is lower than the temperature of the heated first air flow. Mixing of the two air flows lowers the temperature of a vapor entering the user's mouth. In various embodiments, lower temperature of the vapor improves the taste of the vapor. In various embodiments, lower temperature of the vapor provides a smoother "throat hit" to the user. As used herein, "throat hit" may refer to the sensation caused by the vapor and/or volatile substance as it is inhaled by the user. As used herein, a "volatile substance" may refer to nicotine and/or other chemicals comprised by the liquids and/or extracts. In various embodiments, lower temperature of the vapor prevents burning of, and/or discomfort to, the user's lips, tongue, cheeks, and/or mouth.

In various embodiments, simultaneous communication of two, separated air flows to the user's mouth allows the user to take a larger volume of vapor in a single inhalation. Larger inhalation volume may improve the taste of the vapor relative to smaller inhalation volume. Larger inhalation volume may improve the throat hit of the vapor relative to smaller inhalation volume. Larger inhalation volume may allow the vapor to contact more portions of the user's lips, tongue, throat, cheeks, and/or mouth than smaller inhalation volume. Larger inhalation volume may allow the user to inhale more vapor than a smaller inhalation volume. For example, larger inhalation volume may allow the user, at his or her option, to take a direct lung inhale (for example, inhaling vapor directly into the lungs) and/or to take a mouth to lung inhale (for example, sucking vapor into the mouth and subsequently opening the mouth as the vapor and ambient air are inhaled). In various embodiments, optional election of mouth to lung inhalation or direct lung inhalation may be beneficial for users habituated to cigarettes or cigars, for new vaporizer users, or for individuals with impaired lung capacity or hyperinflation of the lungs.

Certain plant materials, extracts, or oils suitable for use in vaporizer pods may be thick, viscous, solid and/or semisolid at ambient temperature. After such plant materials, extracts and oils are disposed in a vaporizer pod, they may collect at or near a heating element and, because they are thick, viscous, solid and/or semisolid, may restrict or prevent airflow through the vaporizer pod and/or into the user's mouth. The vaporizer pod disclosed herein may continue to communicate air through the vaporizer pod and/or into the user's mouth via the second air flow, even when plant materials, extracts or oils disposed within the vaporizer pod become thick, viscous, solid and/or semisolid.

In various embodiments, the vaporizer pod may comprise a filter disposed in the heating element. The filter may be comprised of a heat-conducting material. For example, the filter material may include a porous mesh layer comprising metal, including titanium, copper, tungsten, aluminum, gold, or nickel. The filter may comprise a metal alloy such as a nickel-chromium alloy, iron-chromium-aluminum alloy, stainless steel, zinc alloy, or any other suitable alloy including commercially-available alloys such as Kanthal® wire produced by the Bulten-Kanthal company of Hallstahammar, Sweden. The filter may comprise a heat-conducting ceramic, including molybdenum disilicide ($MoSi_2$), silicon carbide, and/or any other heat-conducting ceramic. Further, the filter may comprise any mineral, metal, alloy, ceramic, composite, or other material suitable for use in the vaporizer pod. In various embodiments, the filter comprises a multitude of holes allowing for vapor to flow from the heating element through the filter and the atomizer channel, to the atomizer channel outlet.

In various embodiments, the vaporizer pod and/or the vaporizer to which it is coupled comprises a pressure sensor. Communication of the second air flow through the vaporizer pod (for example, when a user takes an inhalation from the vaporizer pod) may be detected by the pressure sensor. The pressure sensor may send a signal to a processor and/or a controller that causes the heating element's temperature to increase. An increase in temperature of the heating element may cause the liquids and extracts to aerosolize. In various embodiments, heating of liquids and extracts disposed within the vaporizer pod may be activated through ordinary operation of the vaporizer pod, namely, when a user inhales into the mouth piece attached to the vaporizer pod.

In various embodiments and with reference to FIGS. 1-7, a vaporizer pod 100 comprises a housing 110. Housing 110 may be configured to receive liquids and extracts into a reservoir 111 defined by housing 110. In various embodiments, housing 110 comprises a generally prismatic shape. However, in various embodiments, the housing may comprise a cuboidal shape, spherical shape, conical shape, pyramidal shape, cylindrical shape, hexagonal shape, or any other shape suitable for defining a reservoir. In various embodiments, housing 110 comprises a shape complementary to the shape of a vaporizer, such that vaporizer pod 100 may be disposed at least partially in, or otherwise coupled to, the vaporizer.

Figure 2:
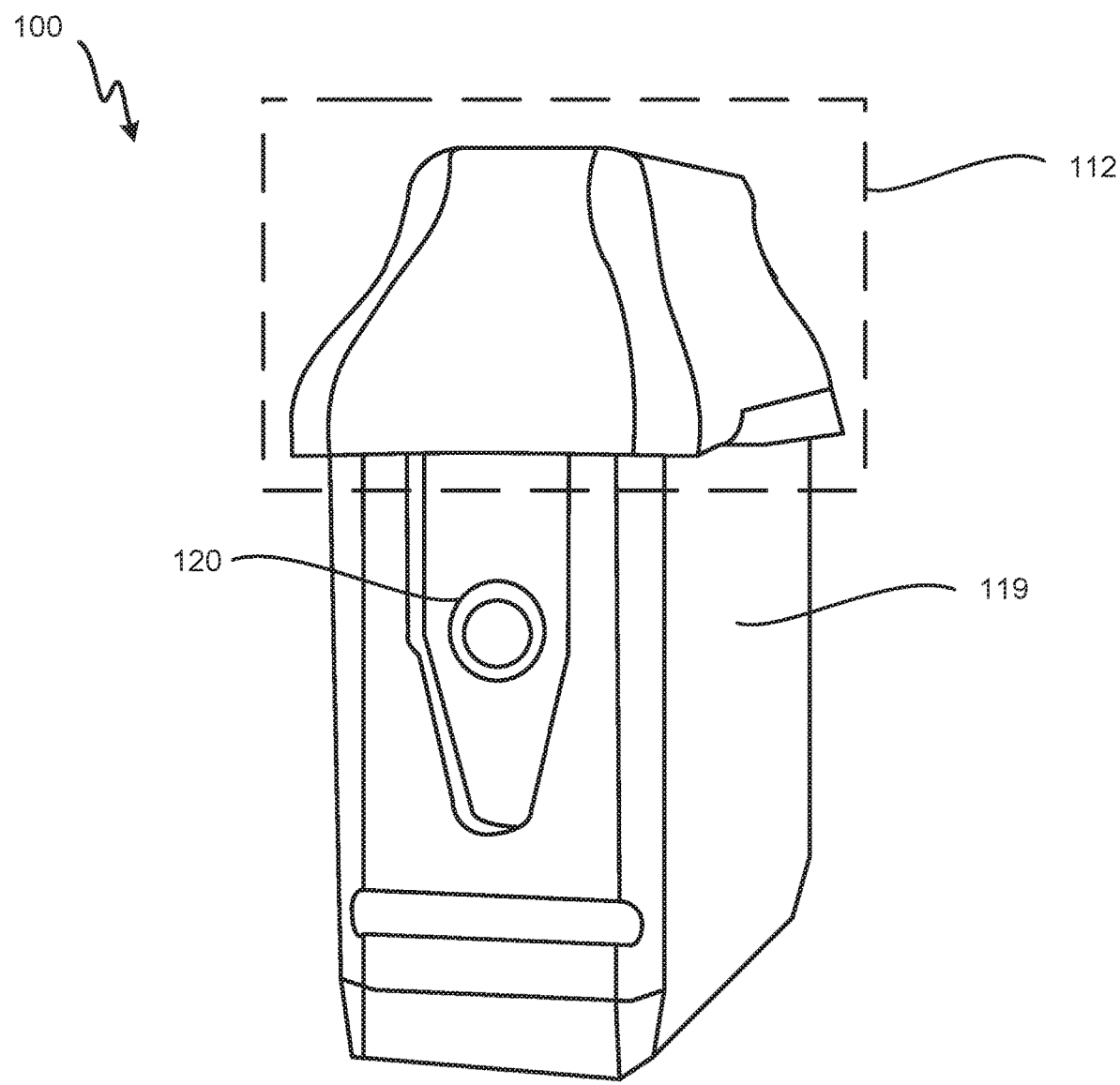
FIG. 2 illustrates a side view of various components of a vaporizer pod in accordance with various embodiments.

In various embodiments, and with specific reference to FIGS. 1-2, housing 110 may comprise component parts. For example, in various embodiments, housing 110 comprises a mouth piece 112, an upper portion 119, and/or one or more base portions (114, 115). However, in various embodiments, the housing is integral. In various embodiments, a contact 116 may be disposed on housing 110. Contact 116 may be coupled to and disposed at least partially in housing 110. In various embodiments, contact 116 is coupled to and disposed in a second base portion 115 of housing 110 such that a contact surface of contact 116 is disposed on an outer, bottom surface of housing 110. In various embodiments, a fill plug 120 may be disposed on housing 110. Fill plug 120 may be coupled to and disposed at least partially in housing 110. In various embodiments, fill plug 120 may be disposed on base portion 114. Fill plug 120 may be coupled to and disposed at least partially in base portion 114.

Mouth piece 112 may be coupled to and/or comprise a portion of housing 110. Mouth piece 112 may be coupled to a top portion of upper portion 119. In various embodiments, mouth piece 112 comprises a contact portion that is configured to be in contact with a user's mouth. For example, mouth piece 112 may be ergonomically shaped for a user's mouth. Mouth piece 112 may extend over upper portion 119 to prevent a user's mouth from touching upper portion 119. For example, mouth piece 112 may be prismatically shaped.

Figure 3:
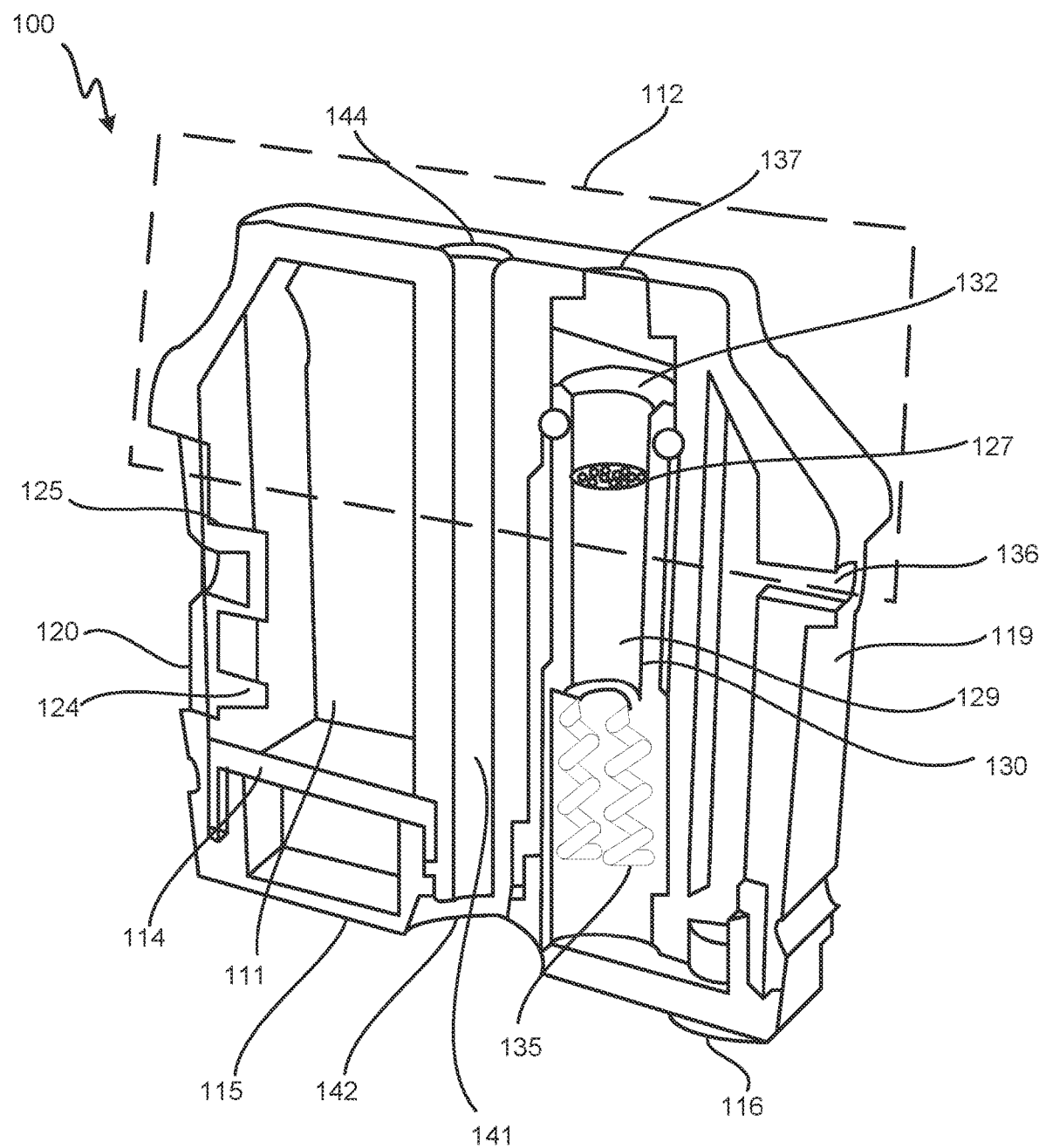
FIG. 3 illustrates a perspective cross section view of a vaporizer pod in accordance with various embodiments.
Figure 4:
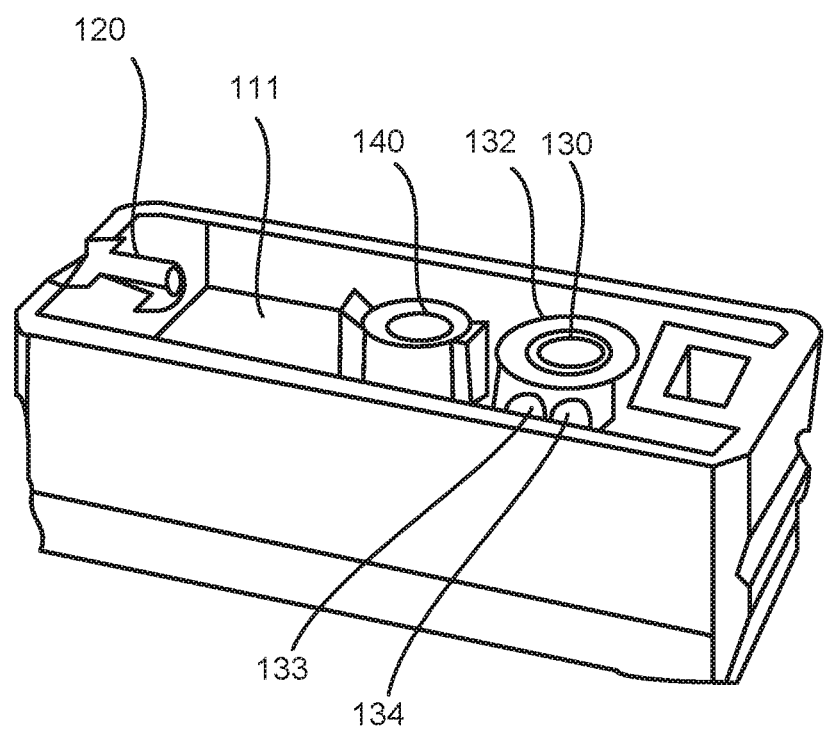
FIG. 4 illustrates a cross section of a vaporizer pod in accordance with various embodiments.
Figure 5:
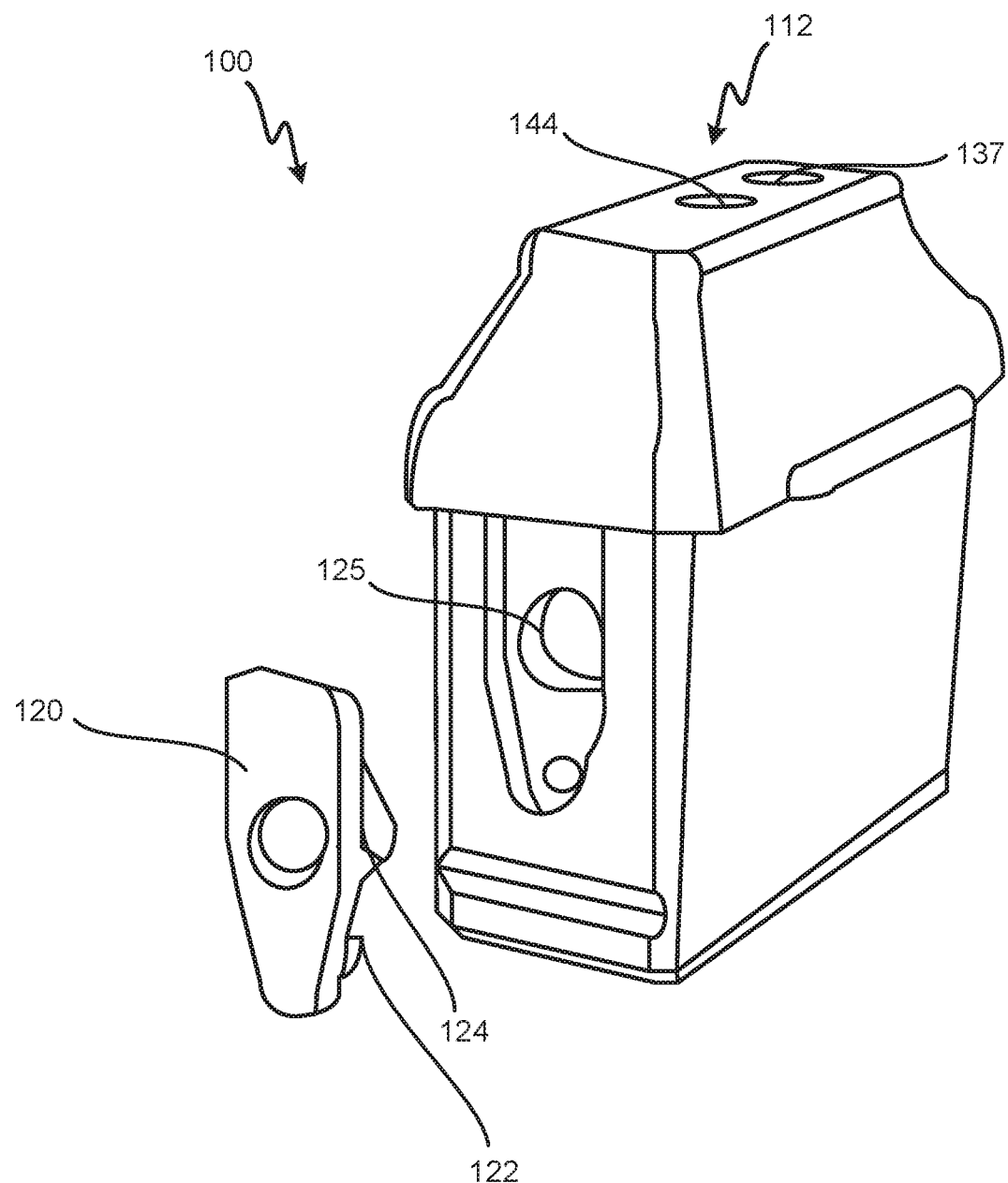
FIG. 5 illustrates an exploded view of various components of a vaporizer pod in accordance with various embodiments.

In various embodiments, and with specific reference to FIGS. 3-5, a central channel outlet 144 may be disposed on, and defined by, mouth piece 112. An atomizer channel outlet 137 may be disposed on, and defined by, mouth piece 112. Central channel outlet 144 and atomizer channel outlet 137 may be disposed in close proximity to one another on mouth piece 112, such that central channel outlet 144 and atomizer channel outlet 137 are configured to be placed in a user's mouth simultaneously. For example, if a user inhales from central channel outlet 144, ambient air may be pulled from central channel inlet 142 to central channel 140 via central air flow 141 to the user's mouth via central channel outlet 144. Further, if a user inhales from atomizer channel outlet 137, ambient air may be pulled from atomizer channel inlet 136 to atomizer channel 130 via atomizer channel airflow 129 to the user's mouth via atomizer channel outlet 137. In various embodiments, central channel outlet 144 and atomizer channel outlet 137 are disposed in a top surface of mouth piece 112. However, central channel outlet 144 and atomizer channel outlet 137 may be disposed on any suitable surface or portion of housing 110.

Central channel inlet 142 may be disposed on, and defined by, housing 110. In various embodiments, central channel inlet 142 is disposed on, and defined by, a second base portion 115 of housing 110. Central channel inlet 142 may be disposed in a bottom surface of housing 110. However, central channel inlet 142 may be disposed on any suitable portion of housing 110.

Housing 110 and/or a base portion (114, 115) thereof may define a portion of central channel 140. Central channel 140 may comprise a channel, tube, hollow cylinder, hose, or other conduit configured to communicate ambient air through vaporizer pod 100, as generally illustrated in the accompanying figures as central air flow 141, and out of vaporizer pod 100 via central channel outlet 144.

In various embodiments, vaporizer pod 100 is configured to direct atomizer air flow 129 from atomizer channel inlet 136, through an atomizer channel 130, to and through atomizer channel outlet 137, and out of vaporizer pod 100. Atomizer channel inlet 136 may be disposed on, and defined by, housing 110. In various embodiments, atomizer channel inlet 136 is disposed on, and defined by, an upper portion 119 of housing 110. Atomizer channel inlet 136 may be disposed in a side surface of upper portion 119. However, atomizer channel inlet 136 may be disposed on any suitable portion of housing 110, upper portion 119, and/or mouth piece 112.

Housing 110 and/or a base portion (114, 115) may defined some or all of atomizer channel 130. Atomizer channel 130 may comprise a channel, tube, hollow cylinder, hose, or other conduit configured to direct ambient air through vaporizer pod 100, as generally illustrated in the accompanying figures as atomizer air flow 129, and into a user's mouth via atomizer channel outlet 137.

In various embodiments, filter 127 may be disposed in and coupled to atomizer channel 130. Filter 127 may comprise a channel, tube, hollow cylinder, hose, or any other form that fits tightly within atomizer channel 130. For example, filter 127 may allow a user to tilt or position the vaporizer pod 100 in a direction other than vertically without allowing liquids or extracts to spill from atomizer channel outlet 137. Filter 127 may comprise a heat-conducting material. Filter 127 may comprise a nonabsorbent material. In various embodiments, filter 127 may be in electrical contact with a heat conductor and/or contact (described hereinafter) as a means to heat or increase a temperature of filter 127. When filter 127 is heated and placed into contact with liquids or extracts disposed in atomizer channel 130, it may provide an additional surface and/or heat source from which for liquids or extracts can aerosolize. Upon contact with heated filter 127, liquids or extracts may aerosolize into vapor. Vaporizer pod 100 comprising filter 127 may provide vapor having an improved concentration of aerosolized liquid and/or extract.

In various embodiments, at least a portion of atomizer channel 130 is defined by column 132. Column 132 may be at least partially disposed in reservoir 111 and may be configured to at least partially segregate reservoir 111 from atomizer channel 130. In various embodiments, column 132 is configured to facilitate contact between ambient air communicated via atomizer air flow 129 and liquids or extracts disposed generally within vaporizer pod 100. Column 132 may further be configured to receive heat conductor 135 and facilitate contact between heat conductor 135 and liquids or extracts disposed generally within vaporizer pod 100. Column 132 may generally comprise a hollow cylindrical shape. However, column 132 may comprise any shape suitable for use in vaporizer pod 100.

Heat conductor 135 may be disposed at least partially within column 132. Heat conductor 135 may be disposed vertically relative to column 132 and/or vaporizer pod 100. Heat conductor 135 may be disposed horizontally relative to column 132 and/or vaporizer pod 100. In various embodiments, heat conductor comprises a generally cylindrical shape or tubular shape, such that fluid (for example, air, vapor, liquids, and the like) may generally pass through heat conductor 135 from a first end to a second end. In various embodiments, heat conductor comprises a material that is sufficiently porous such that fluid (for example, air, vapor, liquids, and the like) may generally pass through heat conductor 135 from a first end to a second end. Heat conductor 135 may comprise a hollow cylinder, a coil, and/or any shape or material suitable for use in vaporizer pod 100, as will be discussed further herein.

In various embodiments, ambient air drawn through atomizer channel inlet 136 enters a portion of housing 110 that is segregated from reservoir 111. In various embodiments, as ambient air is directed along atomizer air flow 129, it is brought into contact with and enters a bottom end of column 132 and/or heat conductor 135. As the ambient air is directed through and/or brought into contact with heat conductor 135, it may be commingled with all or a portion of the liquids or extracts that have evaporated, sublimated, volatilized, and/or otherwise atomized. A vapor that results from such commingling is then directed through a top end of heat conductor 135 and/or column 132, is further directed through filter 127, and is finally directed through atomizer channel outlet 137. The user may inhale the resulting vapor via mouth piece 112 coupled to atomizer channel outlet 137.

Figure 6:
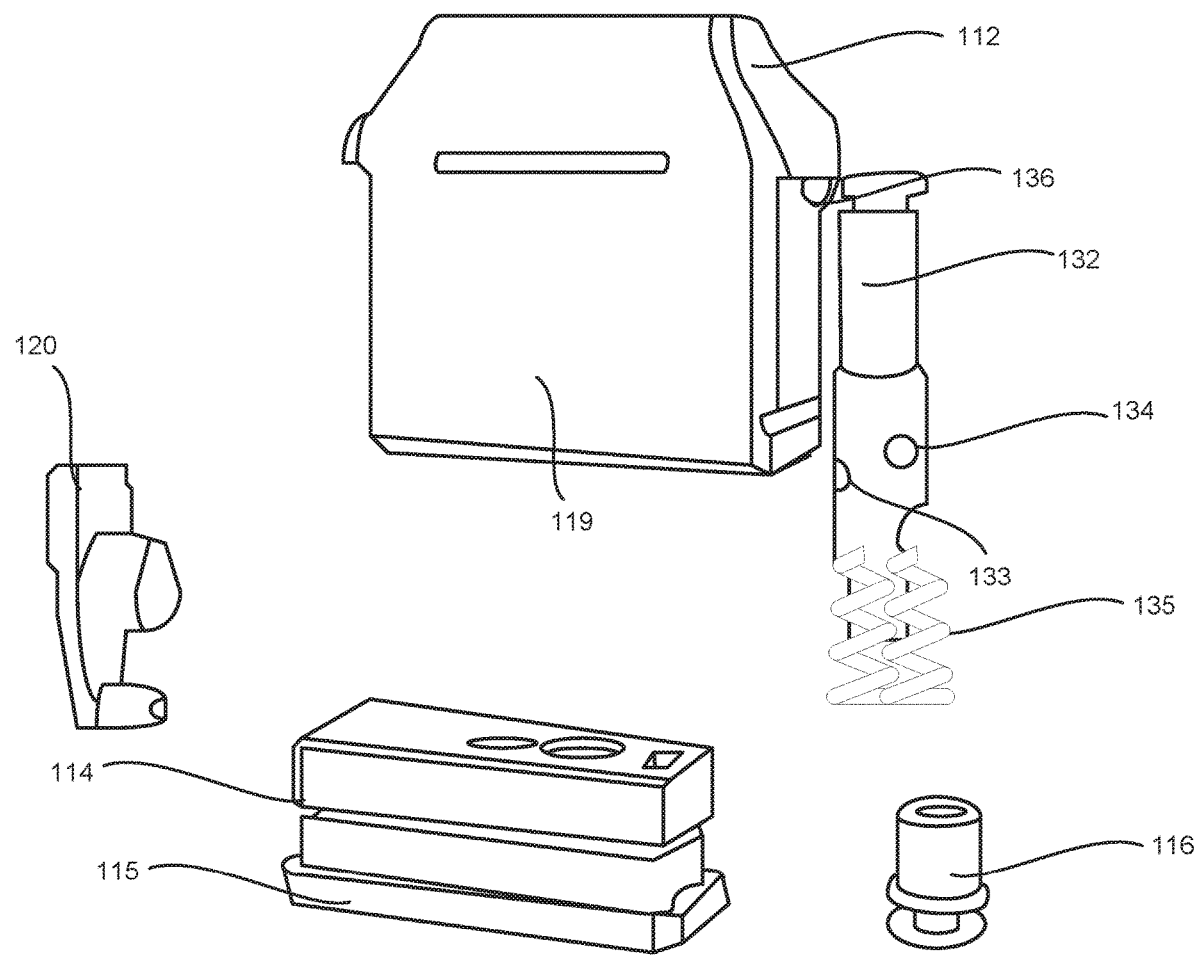
FIG. 6 illustrates an exploded view of various components of a vaporizer pod in accordance with various embodiments.
Figure 7:
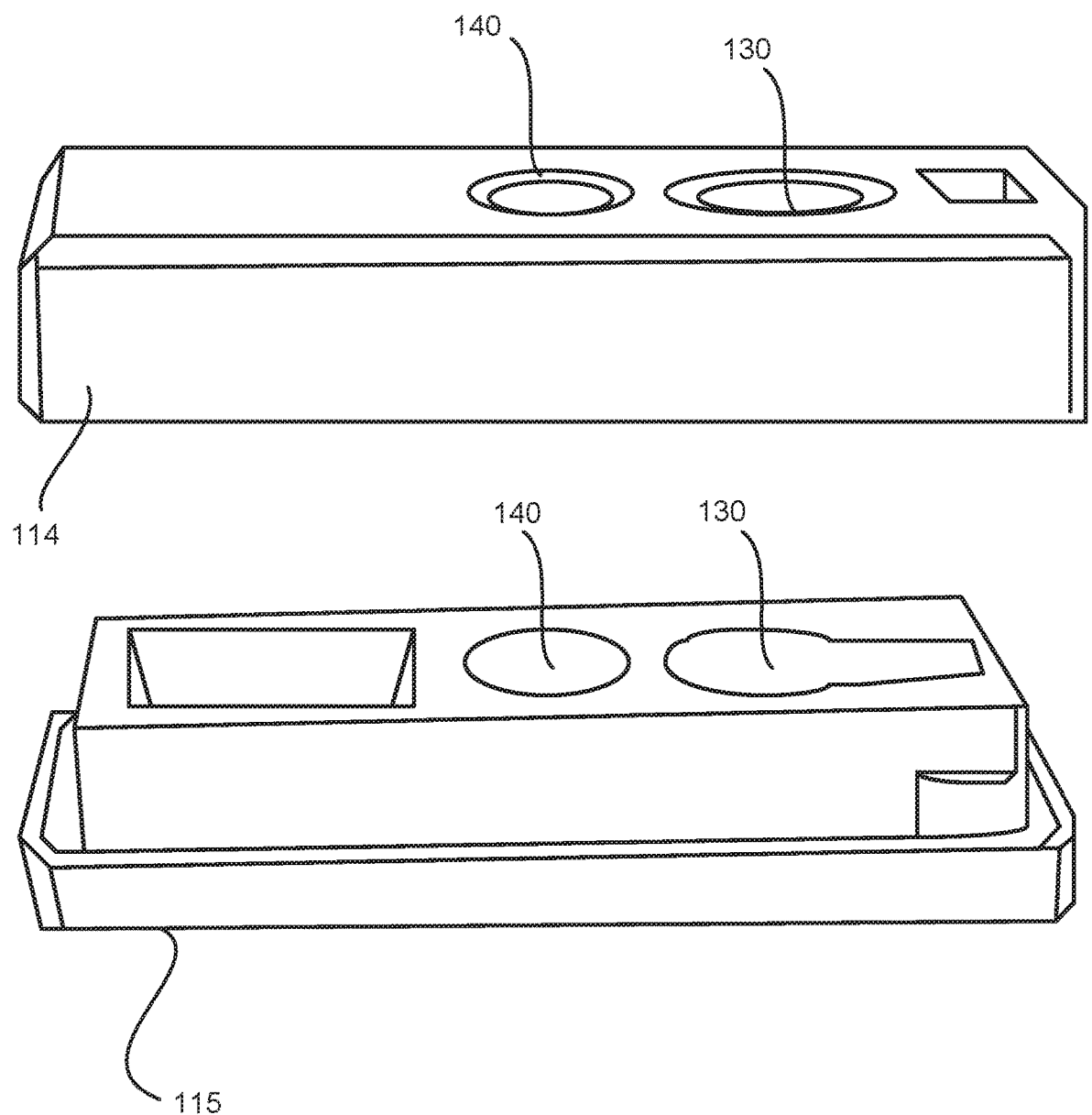
FIG. 7 illustrates an exploded view of a portion of a vaporizer pod in accordance with various embodiments.

In various embodiments, with specific reference to FIG. 6-7, column 132 comprises a first fluid port 133. First fluid port 133 may comprise an aperture, opening, slot, hole, or the like disposed on and defined by a sidewall of column 132. First fluid port 133 may be configured to interface with one or more portions of housing 110 (for example, base portions 114, 115) and may direct the ambient air into contact with heat conductor 135.

In various embodiments, column 132 comprises one or more second fluid ports 134. Second fluid port 134 may comprise an aperture, opening, slot, hole, or the like disposed on and defined by a sidewall of column 132. In various embodiments, second fluid port 134 is disposed above first fluid port 133. In various embodiments, second fluid port 134 is disposed below first fluid port 133. In various embodiments, second fluid port 134 is disposed above first base portion 114. Second fluid port 134 may be configured to allow direction of liquids or extracts from reservoir 111, into column 132, and into contact with heat conductor 135.

Heat conductor 135 may be configured to receive an electrical current from a power source, such as a battery, electric socket, electric generator, or the like. Heat conductor 135 may be configured to transfer heat to liquids or extracts disposed in vaporizer pod 100. In various embodiments, heat conductor 135 may comprise multiple conductors. In various embodiments, heat conductor 135 comprises a wire. In various embodiments, the length of the wire is determined by the size and/or shape of column 132. The length of the wire may be the maximum length capable of being disposed within column 132. In various embodiments, the wire may be oriented within column 132 to form a coil. However, the wire may be oriented within column 132 to form a zig-zag pattern, hairpin pattern, or any other pattern suitable for embedding the wire in the cup. The wire may comprise a diameter of between about 3.26 mm and about 0.07 mm (8 gauge to 40 gauge). The wire may comprise a 26-gauge wire. The wire may comprise a diameter of about 0.40 mm. However, the wire may comprise any diameter suitable for being used in vaporizer pod 100.

In various embodiments, heat conductor 135 comprises a hollow cylindrical shape. In various embodiments, cotton, gauze, a wicking material, and/or a dispersant material is disposed within heat conductor 135. In various embodiments, heat conductor 135 comprises a metal such as titanium, copper, tungsten, aluminum, gold, or nickel. Heat conductor 135 may comprise a metal alloy such as a nickel-chromium alloy, iron-chromium-aluminum alloy, stainless steel, zinc alloy, or any other suitable alloy including commercially-available alloys such as Kanthal® wire produced by the Bulten-Kanthal company of Hallstahammar, Sweden. However, heat conductor 135 may comprise any mineral, metal, alloy, ceramic, composite, or other material suitable for use in vaporizer pod 100. In various embodiments, heat conductor 135 may be selected based on physical properties of vaporizer pod 100. For example, heat conductor 135 may comprise a material having a maximum temperature threshold (based on the voltage applied to it by a power source) below a melting temperature of one or more portions of vaporizer pod 100.

In various embodiments, heat conductor 135 is disposed vertically within column 132 and/or vaporizer pod 100. Stated differently, heat conductor 135 may be disposed with a first end below a second end, and may be configured to direct a fluid in an upward direction relative to vaporizer pod 100. In various embodiments, vertical disposition and/or orientation may allow heat conductor 135 to be larger and/or longer than would be possible with a horizontal disposition and/or orientation. A larger and/or longer heat conductor 135 may improve and/or increase evaporation, sublimation, volatilization, and/or atomization of liquids or extracts. A larger and/or longer heat conductor 135 may improve the flavor of vapor produced by the vaporizer. A larger and/or longer heat conductor 135 may improve the throat hit produced by the vaporizer. A larger and/or longer heat conductor 135 may allow the vaporizer to operate at a lower relative temperature.

In various embodiments, heat conductor 135 is disposed horizontally within column 132 and/or vaporizer pod 100. Stated differently, heat conductor 135 may be disposed with a first end level to a second end, and may be configured to direct a fluid in an upward direction relative to vaporizer pod 100. In various embodiments, a lower portion of column 132 may be horizontal. The lower portion of column 132 may be parallel and/or disposed on base portion 114. A vertical portion of column 132 may intersect with the horizontal lower portion of column 132 at a perpendicular angle. In various embodiments, horizontal disposition and/or orientation may allow heat conductor 135 to be larger and/or longer than would be possible with a vertical disposition and/or orientation. A larger and/or longer heat conductor 135 may improve and/or increase evaporation, sublimation, volatilization, and/or atomization of liquids or extracts. A larger and/or longer heat conductor 135 may improve the flavor of vapor produced by the vaporizer. A larger and/or longer heat conductor 135 may improve the throat hit produced by the vaporizer. A larger and/or longer heat conductor 135 may allow the vaporizer to operate at a lower relative temperature.

In various embodiments, heat conductor 135 may be configured to receive a voltage of between about 1.5V and about 8V. More preferably, heat conductor 135 may be configured to receive a voltage of between about 2V and about 5V. In various embodiments, heat conductor 135 is configured to receive a voltage of about 3V to about 4V when the heating assembly is used with concentrated liquids, extracts, or other concentrates. In various embodiments, heat conductor 135 is configured to receive a voltage of about 2.5V to about 3.5V when the heating assembly is used with plant-based oils. However, heat conductor 135 may receive any voltage suitable for use in vaporizer pod 100.

In various embodiments, heat conductor 135 is mechanically and/or electrically coupled to contact 116. Contact 116 may be coupled to and disposed at least partially in housing 110. In various embodiments, contact 116 is coupled to and disposed in a second base portion 115 of housing 110 such that a contact surface of contact 116 is disposed on an outer, bottom surface of housing 110. The contact surface of contact 116 may be configured to interface with, and receive a current from a power source.

Contact 116 may be configured to communicate a current from a power source to heat conductor 135. In various embodiments, contact 116 comprises an electrically conductive pin. In various embodiments, contact 116 may also comprise a contact tip, socket, stamping, sheet, wire, and/or wheel. Contact 116 may comprise copper. Contact 116 may be electroplated with an electrically conductive material. In various embodiments, contact 116 comprises gold-plated copper. However, contact 116 may comprise any suitable metal, alloy, or other conductive material, and may be electroplated with any suitable metal, alloy, or other conductive material. In various embodiments, contact 116 may comprise a 510 thread connector, an 808 thread connector, an eGo™ connector, or any other electrical connector suitable to communicate an electrical current from a power source to heat conductor 135.

In various embodiments, vaporizer pod 100 further comprises a fill aperture 125 configured to allow a user to fill reservoir 111 with liquids or extracts. Fill aperture 125 may be disposed on, and defined by, housing 110. In various embodiments, fill aperture 125 is disposed on, and defined by, a side wall of upper portion 119. Fill aperture 125 may comprise a circular, ovoid, square, or any other suitable shape. In various embodiments, fill aperture 125 comprises a shape complimentary to a plug portion 124 of fill plug 120 that is configured to be force fit into fill aperture 125.

Fill plug 120 may further comprise an anchor 122 configured to secure a portion of fill plug 120 to housing 110, while allowing plug portion 124 to be optionally remove from and replaced within fill aperture 125. In various embodiments, fill plug 120 is configured to seal or otherwise prevent fluid from exiting reservoir 111 through fill aperture 125. Further, fill plug 120 may be configured to seal fluid from exiting reservoir 111 via any other method appropriate for sealing, including a gasket, adhesive, and/or any other type of mechanical seal appropriate for use with vaporizer pod 100.

In various embodiments, a vaporizer pod as described herein may be disposed in a vaporizer. The vaporizer may comprise a body configured to partially or completely enclose the vaporizer pod. In various embodiments, the vaporizer further comprises a power source, such as a battery. In various embodiments, the battery comprises a lithium ion battery. In various embodiments, the battery is rechargeable. However, the battery may comprise an alkaline battery, nickel metal hydride battery, nickel cadmium battery, or any other suitable battery. In various embodiments, the battery comprises between about 200 mAh and about 5000 mAh. However, the battery may comprise any suitable capacity. In various embodiments, the battery is configured to deliver a voltage of between about 2V and about 5V.

The battery may be disposed at least partially within the body. The battery may be mechanically and/or electrically coupled to contact 116 of vaporizer pod 100. The battery may be directly coupled to a first end and/or a second end of heat conductor 135. The battery may be indirectly coupled to contact 116 via one or more intervening components of the vaporizer and/or the vaporizer pod 100.

In various embodiments, the battery may be in communication with a controller disposed within the housing. The controller may comprise a programmable circuit board. The controller may comprise a processor configured to implement various logical operations in response to execution of instructions, for example, instructions stored on a non-transitory, tangible, computer-readable medium. In various embodiments, the controller may be configured to provide commands in response to variable and non-variable inputs. Variable inputs may include a voltage applied by the power source and/or a signal provided by a sensor coupled to the vaporizer or a vaporizer pod. For example, in various embodiments, a sensor in fluid communication with central channel 140 is configured to detect a change in air pressure associated with a user's drag of air from the vaporizer pod mouth piece. In response, the sensor may send a signal to the controller, which may cause the battery to apply a voltage directly to contact 116 and/or indirectly to heat conductor 135. Non-variable inputs may include the coil material, the coil length, diameter, thickness, or gauge, the reservoir volume, and/or other dimensions and characteristics of the vaporizer pod.

In various embodiments, one or more portions of the vaporizer pod 100 comprises a biodegradable material. For example, housing 110, mouthpiece 112, base portion (114, 115), and/or fill plug 120 may comprise a biodegradable material. However, in various embodiments, any portion of vaporizer pod 100 may comprise a biodegradable material.

It will be apparent to those skilled in the art that various modifications and variations can be made to the present disclosure without departing from the spirit or scope of the disclosure. Thus, it is intended that the present disclosure cover the modifications and variations of this disclosure provided they come within the scope of the appended claims and their equivalents.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all of the claims.

It should be understood that the detailed description and specific examples, indicating exemplary embodiments, are given for purposes of illustration only and not as limitations. Many changes and modifications may be made without departing from the spirit thereof, and principles of the present disclosure include all such modifications. Corresponding structures, materials, acts, and equivalents of all elements are intended to include any structure, material, or acts for performing the functions in combination with other elements. Reference to an element in the singular is not intended to mean "one and only one" unless explicitly so stated, but rather "one or more." Moreover, when a phrase similar to "at least one of A, B, or C" or "at least one of A, B, and C" is used in the claims or the specification, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. A vaporizer pod comprising:
a reservoir defined by, and disposed within a housing, wherein the housing defines a central channel extending between a central channel inlet and a central channel outlet;
a column disposed within the housing, the column including an upper portion;
an atomizer channel extending between an atomizer channel inlet and an atomizer channel outlet;
a heat conductor disposed within the column; and
a filter disposed within the column, the filter comprising a heat-conducting material, the filter coupled to and disposed within the upper portion of the column.

2. The vaporizer pod of claim 1, wherein the atomizer channel is defined by the housing and the column.

3. The vaporizer pod of claim 1, wherein the central channel outlet and the atomizer channel outlet are disposed in a mouth piece.

4. The vaporizer pod of claim 1, further comprising a fill plug coupled to and disposed at least partially within a fill aperture defined by the housing.

5. The vaporizer pod of claim 4, wherein the fill aperture is defined by a side wall of the housing.

6. The vaporizer pod of claim 1, wherein a base portion of the housing defines at least a portion of the reservoir, and wherein the column is disposed at least partially within the base portion.

7. The vaporizer pod of claim 4, wherein:
the reservoir is in fluid communication with the heat conductor through a first fluid port defined by the column, and
the atomizer channel inlet is in fluid communication with the atomizer channel outlet through a second fluid port defined by the column.

8. The vaporizer pod of claim 1, wherein the filter comprises a porous mesh.

9. The vaporizer pod of claim 8, wherein the filter comprises a metal.

10. The vaporizer pod of claim 1, wherein the filter comprises a ceramic.

11. The vaporizer pod of claim 1, wherein the filter is nonabsorbent.

12. The vaporizer pod of claim 1, wherein the heat conductor comprises a wire.

13. The vaporizer pod of claim 1, wherein the heat conductor comprises a coil.

14. The vaporizer pod of claim 1, wherein the heat conductor may be a hollow cylindrical shape.

15. A vaporizer pod comprising:
an electrical contact configured to communicate a current from a power source;
a reservoir defined by, and disposed within a housing, wherein the housing comprises:
a central channel inlet, a central channel outlet, and a central channel disposed therebetween and defined by the housing;
an atomizer channel inlet, an atomizer channel outlet, and an atomizer channel disposed therebetween, wherein the atomizer channel is defined by the housing and a column disposed within the housing wherein the central channel outlet and the atomizer channel outlet are disposed in a mouth piece;
a heat conductor disposed within the column, wherein the heat conductor is in fluid communication with the reservoir and in electrical communication with the electrical contact;
a heat-conducting filter disposed within the column; and
a fill plug coupled to and disposed at least partially within a fill aperture defined by the housing.

16. A vaporizer comprising:
an electrical contact of a vaporizer pod, the electrical contact configured to communicate a current from a power source, wherein the vaporizer pod comprises:
a reservoir defined by, and disposed within a housing, the electrical contact disposed on the housing, wherein the housing comprises:
a central channel inlet, a central channel outlet, and a central channel disposed therebetween and defined by the housing;
an atomizer channel inlet, an atomizer channel outlet, and an atomizer channel disposed therebetween and defined by the housing and a column disposed within the housing, wherein the central channel outlet and the atomizer channel outlet are disposed in a mouth piece;
a heat conductor disposed within the column, wherein the heat conductor is in fluid communication with the reservoir and in electrical communication with the electrical contact;
a heat-conducting filter disposed within the column; and
a fill plug coupled to and disposed at least partially within a fill aperture defined by the housing.

17. The vaporizer pod of claim 15, wherein the heat-conducting filter is in electrical communication with the heat conductor.

18. The vaporizer of claim 16, wherein the heat-conducting filter is in electrical communication with the heat conductor.

19. A vaporizer pod comprising:
a reservoir defined by, and disposed within a housing, wherein the housing defines a central channel extending between a central channel inlet and a central channel outlet;
a column disposed within the housing;
an atomizer channel extending between an atomizer channel inlet and an atomizer channel outlet, wherein the central channel outlet and the atomizer channel outlet are disposed in a mouth piece; and
a heat conductor disposed within the column; and a filter disposed within the column, the filter comprising a heat-conducting material.

20. A vaporizer pod comprising:
a reservoir defined by, and disposed within a housing, wherein the housing defines a central channel extending between a central channel inlet and a central channel outlet;
a column disposed within the housing;
an atomizer channel extending between an atomizer channel inlet and an atomizer channel outlet;
a heat conductor disposed within the column;
a filter disposed within the column, the filter comprising a heat-conducting material; and
a fill plug coupled to and disposed at least partially within a fill aperture defined by the housing.

* * * * *